United States Patent [19]

Hall et al.

[11] Patent Number: 4,695,663

[45] Date of Patent: Sep. 22, 1987

[54] PRODUCTION OF AROMATICS FROM HYDROCARBON FEEDSTOCK

[75] Inventors: Antony H. P. Hall, Cobham; John J. McCarroll, Camberley, both of England

[73] Assignee: The British Petroleum Company p.l.c., London, England

[21] Appl. No.: 891,740

[22] Filed: Jul. 30, 1986

[30]     Foreign Application Priority Data

Aug. 21, 1985 [GB]  United Kingdom ................. 8520977

[51] Int. Cl.$^4$ ............................................... C07C 2/00
[52] U.S. Cl. .................................... 585/417; 585/415; 585/419; 585/500; 585/943
[58] Field of Search ............... 585/407, 415, 417, 419, 585/500, 943

[56]                References Cited

U.S. PATENT DOCUMENTS 3,760,024  9/1973  Cattanach .......................... 585/415
3,775,561  11/1973  Kaiding et al. ..................... 585/417
4,497,970  2/1985  Young ................................ 585/417

FOREIGN PATENT DOCUMENTS 747847  7/1980  U.S.S.R. ............................. 585/500

Primary Examiner—William R. Dixon, Jr.
Assistant Examiner—Cynthia A. Prezlock
Attorney, Agent, or Firm—Brooks Haidt Haffner & Delahunty

[57]                ABSTRACT

This invention relates to a process for producing aromatic hydrocarbons from a feedstock containing a major proportion of methane. The feedstock, in the vapor phase and in the absence of oxygen, is brought into contact with an aluminosilicate at a temperature from 650° C.–800° C. The feedstock may optionally contain ethane.

10 Claims, No Drawings

PRODUCTION OF AROMATICS FROM HYDROCARBON FEEDSTOCK

The present invention relates to a process for producing liquids rich in aromatic hydrocarbons from a hydrocarbon feedstock containing a major proportion of methane.

Hitherto synthetic routes to producing aromatics from open chain hydrocarbons have started from feedstocks which have at least two carbon atoms. Such feedstocks are initially dimerised or oligomerised and the dimerised or oligomerised product is subsequently cyclised over a variety of catalysts at temperatures in the region of 500°–600° C. Such processes are described for example in our British Pat. Nos. 1507778 and 1561590. According to the British Pat. No. 1561590 a gallium catalyst supported on an aluminosilicate in which the ratio of silica to alumina is between 20:1 and 70:1 is used.

It has now been found that aromatics may be produced from hydrocarbon feedstocks containing less than two carbon atoms.

Accordingly, the present invention is a process for producing liquids rich in aromatic hydrocarbons comprising bringing into contact in the vapour phase and in the absence of oxygen at a temperature between 650° C. and 800° C. a hydrocarbon feedstock containing a major proportion of methane with a catalyst composition comprising an aluminosilicate having silica to alumina in a molar ratio of at least 5:1.

The hydrocarbon feedstock has at least 50% w/w, preferably at least 70% w/w of methane and may be admixed with $C_2$ hydrocarbons. The $C_2$ hydrocarbon in the feedstock, if any, may be ethane, ethylene or mixtures thereof. The feedstock may contain in addition other open chain hydrocarbons containing between 3 and 8 carbon atoms as coreactants. Specific examples of such additional coreactants are propane, propylene, n-butane, isobutane, n-butenes and isobutene.

The aluminosilicate in the catalyst composition may be suitably zeolites e.g. those having an MFI type structure (cf. "Chemical Nomenclature, and Formulation of Compositions, of Synthetic and Natural Zeolites," IUPAC yellow booklet, 1978, and zeolite structure types published by The Structure Commission of the International Zeolite Association entitled "Atlas of Zeolite Structure Types", by Meier, W. M. and Olsen, D. H. (1978), distributed by Polycrystal Book Service, Pittsburgh, Pa, USA). The zeolites suitably have a silica to alumina ratio from 20:1 to 200:1 and may be represented by the general formula $M_{2/n}O \cdot Al_2O_3 \cdot ySiO_2 zH_2O$ wherein M is a cation which is a positively charged ion selected from a metal ion or an organic ion of valence n and a proton, y is an integer greater than 5 and z is from 0 to 40. The metal cation, M, is preferably an alkali metal or alkaline earth metal ion, preferably sodium or potassium ions. The organic cations may be represented by the formula $R^1R^2R^3R^4N^+$ or by an ion derived from the amine $R^1R^2R^3N$, the diamine $R^1R^2N(CH_2)_xNR^3R^4$ or pyrrolidine where $R^1R^2R^3$ and $R^4$ may be H, $CH_3$, $C_2H_5$, $C_3H_7$, $C_4H_9$ or $-CH_2CH_2OH$ and x equals 2, 3, 4, 5 or 6. A typical example of an MFI zeolite is ZSM-5 although other zeolites, for example ZSM-8, ZSM-11, ZSM-12 and ZSM-35 may also be used. These zeolites are extensively described in a number of publications including U.S. Pat. No. 3970544 (Mobil). These zeolites are ususally produced from a silica source, an alumina source, an alkali metal hydroxide and a nitrogen containing base as template. The nitrogen-containing base may be organic such as an alkanolamine, for example diethanolamine or, inorganic e.g. ammonia. Zeolites made in this manner are described in our published European Patent Application Nos. 0002899, 0002900 and 0030811. Zeolites derived by the process of EP-A-30811 are preferred.

The activity of the aluminosilicate used as catalyst may be enhanced by loading it with a gallium compound or gallium oxide.

Methods of loading zeolites with gallium are well known and are published for instance in our EP-A-24930. The amount of gallium, if any, present in the catalyst compositions may vary for instance between 0.05% and 10% by weight of the total aluminosilicate in the catalyst composition. The gallium loaded aluminosilicate thus obtained may be combined with a porous matrix, e.g. silica or alumina or other inorganic compositions to improve the mechanical strength of the catalyst.

The catalyst composition whether or not loaded with gallium may be treated prior to contact with the hydrocarbon feedstock. The treatment may be carried out by heating the catalyst at a temperature from 400° C. to 850° C., preferably from 500° C. to 750° C. Treatment may be carried out in an atmosphere of hydrogen, air or a gas inert under the reaction conditions such as nitrogen but preferably in an atmosphere containing oxygen. The gas may contain or consist of steam. The treatment may be carried out in the reactor itself prior to the reaction. The catalyst composition is suitably used in a fixed bed, a moving bed or a fluidised bed.

The hydrocarbon feedstock is thereafter contacted in the vapour phase with the catalyst composition at a temperature from 650° C. to 800° C. preferably from 680° C. to 750° C. in an inert atmosphere in the absence of oxygen. The inert atmosphere may be provided by a gas inert under the reaction conditions such as nitrogen. In fact, once the reactor has been initially flushed with an inert gas such as nitrogen to remove any oxygen or oxidising gases, there is no need to add further amounts of the inert gas to the reaction system. Any unreacted hydrocarbon feedstock and by-products recovered from the reaction products may be recycled to the aromatisation reaction.

The reaction is suitably carried out at a pressure from 1–100 bar, preferably from 2–20 bar.

The WHSV of the reactant hydrocarbon feedstock over the catalyst composition is suitably not greater than 5 and is preferably from 0.1–5.

The invention is further illustrated with reference to the following Examples.

EXAMPLE 1

A sample of an MFI type zeolite containing ammonium ions (prepared according to the general process of our published EP-A-0030811) was washed with dilute nitric acid and dried under vacuum. A portion of the dried material was then refluxed with a solution of gallium nitrate. The gallium loaded zeolite was washed with water, dried and bound with sufficient 'Ludox AS-40' (Registered Trade Mark) to give a catalyst containing 25% of silica binder. The bound catalyst had a gallium content of 0.7% w/w and was crushed and sieved to give 12/30 BSS mesh granules. A portion of the granules was then loaded into a tubular furnace and treated with 5% v/v of steam in air at 550° C. for 2 hours.

Methane was passed at 3 g/h through a reactor containing 6 g of the above catalyst maintained at 700° C. and a pressure of 7 bar absolute. A sample of the vapour stream from the reactor was analysed by on-line dual column gas chromatography (POROPAK QS and OV101 silicone oil columns) which showed that 3.8% of the methane had been converted. The selectivity to aromatics, defined as $$\frac{\text{wt of aromatics produced}}{\text{wt of methane converted}} \times 100$$

was 51%. Small quantities of ethane and ethylene were also formed.

EXAMPLE 2

Methane was passed at 3 g/h through a reactor containing a fresh 6 g portion of the gallium loaded bound, sieved catalyst as in Example 1 above, maintained at 750° C. and a pressure of 7 bar absolute. Analysis as in Example 1 above showed that 6.3% of the methane had been converted with a 40% selectivity to aromatics. The aromatics consisted substantially of benzene and naphthalene.

EXAMPLE 3

The hydrogen form of a zeolite was prepared by exchanging the parent material (prepared according to our published EP-A-0030811) with ammonium nitrate solution followed by calcination. The zeolite was bound with silica (25%), crushed, sieved to 12/30 mesh and treated with 5% v/v of steam in air at 550° C. for 2 hours. Methane was passed at 1.75 g/h through a bed containing 3.5 g of the silica bound catalyst maintained at 700° C./7 bar absolute. Analysis by GC as in Example 1 above showed that 1.8% of the methane had been converted with a selectivity to aromatics of 21% by weight.

COMPARATIVE TEST (NOT ACCORDING TO THE INVENTION)

Methane was passed at 3 g/h through the reactor used in the above Examples, packed with crushed and sieved 12/30 mesh ceramic beads maintained at 700° C. and a pressure of 7 bar absolute. Analysis of the product stream from the reactor by GC as in Example 1 above showed that approximately 0.3% of the methane had been decomposed; with hydrogen being the only product observed.

EXAMPLE 4

A sample of parent material (prepared according to the general procedure of our published EP-A-0030811) was refluxed with 1 M ammoniated ammonium nitrate solution, filtered, washed and dried. This procedure was repeated a second time. This material was then impregnated with gallium nitrate solution.

The gallium loaded zeolite was washed, dried and bound with silica (25%), crushed and sieved to 12/30 mesh. A portion of these granules was then loaded into a tubular furnace and treated with dry air at 750° C. for 4 hours. The finished catalyst had 0.8% w/w gallium.

Methane was passed at 5 g/h through a reactor containing a 5 g portion of the catalyst, maintained at 750° C./7 bar absolute. Analysis by GC as in Example 1 above showed that 4.9% w/w of the methane had been converted with selectivity to aromatics of 48% by weight.

We claim:

1. A process for producing liquids rich in aromatic hydrocarbons comprising bringing into contact in the vapour phase and in the absence of oxygen at a temperature between 650° C. and 800° C. a hydrocarbon feedstock containing greater than 50% w/w of methane with a catalyst composition comprising an aluminosilicate having silica to alumina in a molar ratio of at least 5:1.

2. A process according to claim 1 wherein the hydrocarbon feedstock contains at least 70% w/w of methane.

3. A process according to claim 1 wherein the hydrocarbon feedstock comprises a mixture of methane and $C_2$ hydrocarbons.

4. A process according to claim 1 wherein the aluminosilicate in the catalyst composition is a zeolite having an MFI type structure.

5. A process according to claim 1 wherein the catalyst composition comprises an aluminosilicate having a silica to alumina molar ratio of at least 5:1 and is loaded with a gallium compound or gallium oxide.

6. A process according to claim 1 wherein the catalyst composition is treated by heating at a temperature from 400° to 750° C. prior to contact with the hydrocarbon feedstock.

7. A process according to claim 6 wherein the catalyst composition is treated in an atmosphere containing oxygen.

8. A process according to claim 1 wherein the hydrocarbon feedstock is brought into contact with the catalyst composition at a temperature from 680° to 750° C. in the vapour phase in the absence of oxygen.

9. A process according to claim 1 wherein the reaction is carried out at a pressure from 1-100 bar.

10. A process according to claim 1 wherein the WHSV of the reactant hydrocarbon feedstock over the catalyst composition is not greater than 5.

* * * * *